United States Patent [19]

Murry et al.

[11] 4,180,074
[45] Dec. 25, 1979

[54] DEVICE AND METHOD FOR APPLYING PRECISE IRRIGATION, ASPIRATION, MEDICATION, ULTRASONIC POWER AND DWELL TIME TO BIOTISSUE FOR SURGERY AND TREATMENT

[75] Inventors: Edward J. Murry, Palos Park; Joseph F. Brumbach, Niles, both of Ill.

[73] Assignee: Fibra-Sonics, Inc., Chicago, Ill.

[21] Appl. No.: 777,582

[22] Filed: Mar. 15, 1977

[51] Int. Cl.² ............................................. A61M 1/00
[52] U.S. Cl. .................................. 128/276; 128/305; 128/213 R; 128/274
[58] Field of Search ............... 128/230, 234, 240, 276, 128/277, 278, DIG. 3, 303.13, 303.14, 305, 348, 349 BV, 349 R, 347, 247

[56] References Cited

U.S. PATENT DOCUMENTS

| | | | |
|---|---|---|---|
| 2,733,713 | 2/1956 | Kabnick | 128/230 |
| 3,191,600 | 6/1965 | Everett | 128/276 |
| 3,297,558 | 1/1967 | Hillquist | 128/278 |
| 3,502,097 | 3/1970 | Muller | 128/348 |
| 3,543,752 | 12/1970 | Hesse et al. | 128/230 |
| 3,547,119 | 12/1970 | Hall | 128/348 |
| 3,693,613 | 9/1972 | Kelman | 128/278 |
| 3,734,099 | 5/1973 | Bender et al. | 128/305 |
| 3,812,855 | 5/1974 | Banko | 128/276 |
| 3,920,014 | 11/1975 | Banko | 128/230 |
| 4,002,169 | 1/1977 | Cupler | 128/276 |

OTHER PUBLICATIONS

Page, Robert N., Jr. M.D.; *Maintenance of the Anterior Chamber in Intraocular Surgery: Instruments and Techniques;* from 1968 Transactions of the Pacific Coast Oto-Ophthalmological Society.

Primary Examiner—Robert W. Michell
Assistant Examiner—Arthur S. Rose
Attorney, Agent, or Firm—Hill, Van Santen, Steadman, Chiara & Simpson

[57] ABSTRACT

Apparatus and method for applying aspiration, irrigation, medication and ultrasonic power and dwell time to biotissue for surgery and treatment wherein the pressure for both aspirating and irrigating is precisely and accurately maintained by the use of a differential valve and a control reservoir which is generally much larger than the biotissue cavity to be operated on and wherein the pressures for irrigation, apiration, medication and the application of the amplitude and dwell time of ultrasonic energy can be precisely controlled, externally, to the patient.

15 Claims, 18 Drawing Figures

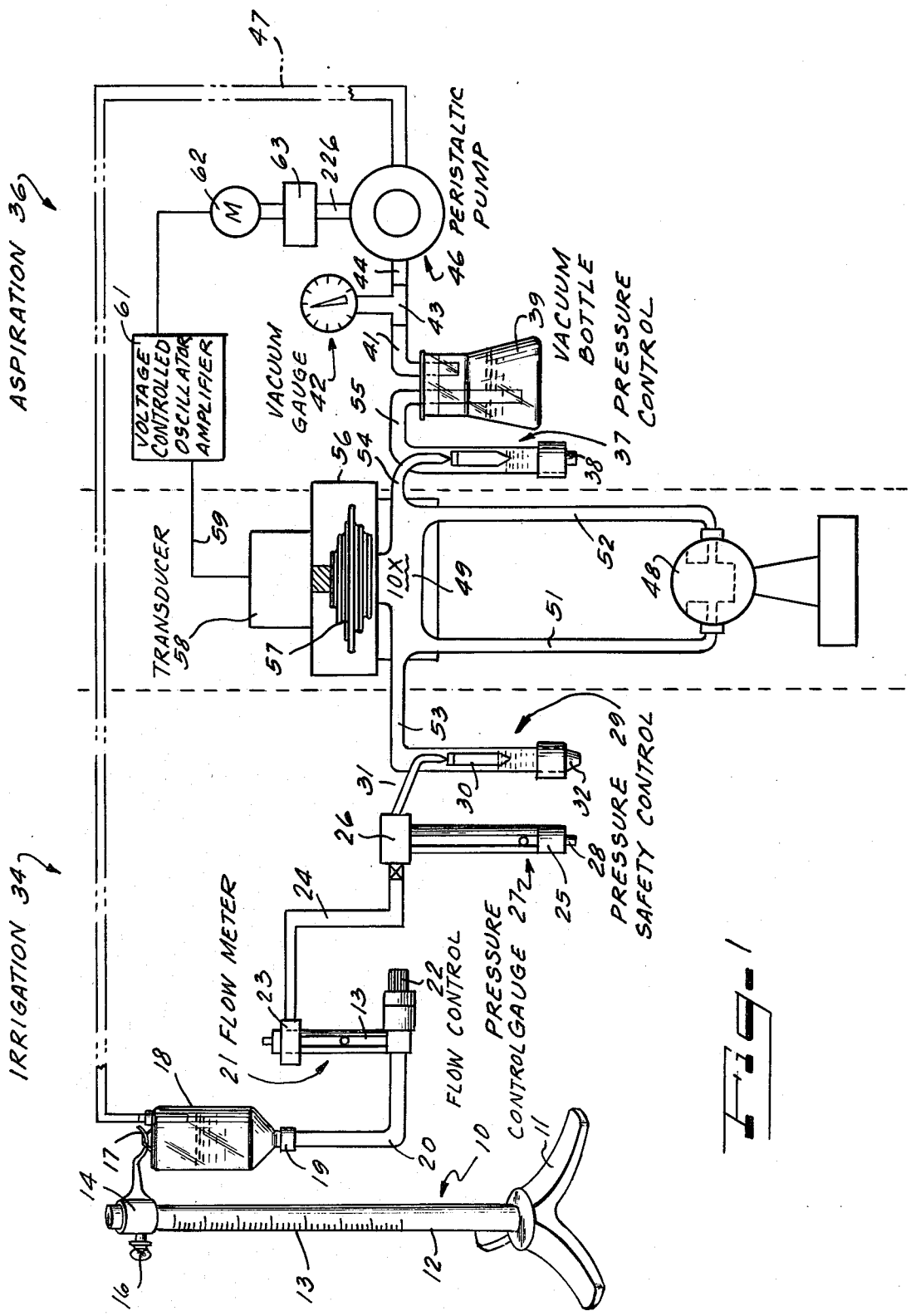

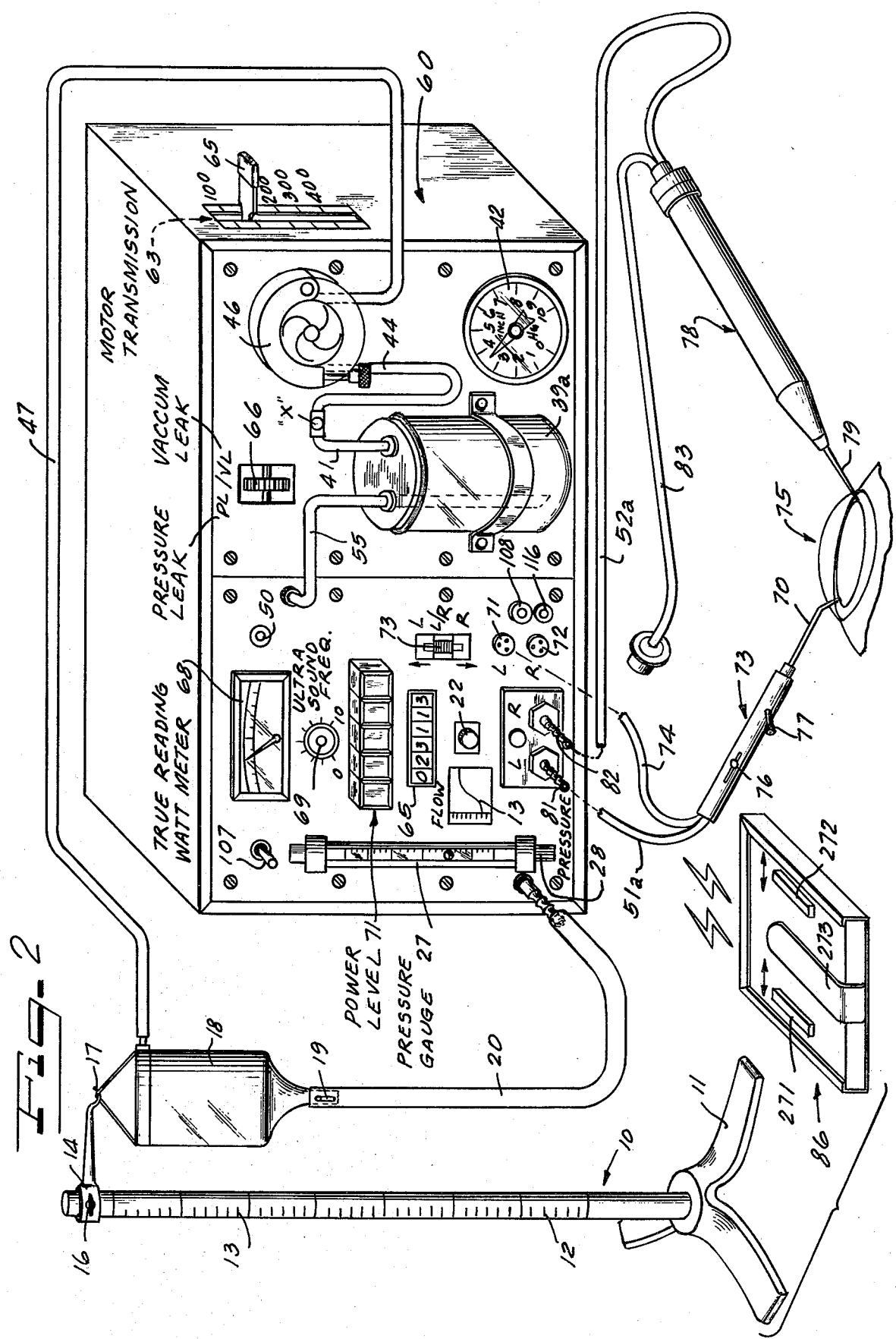

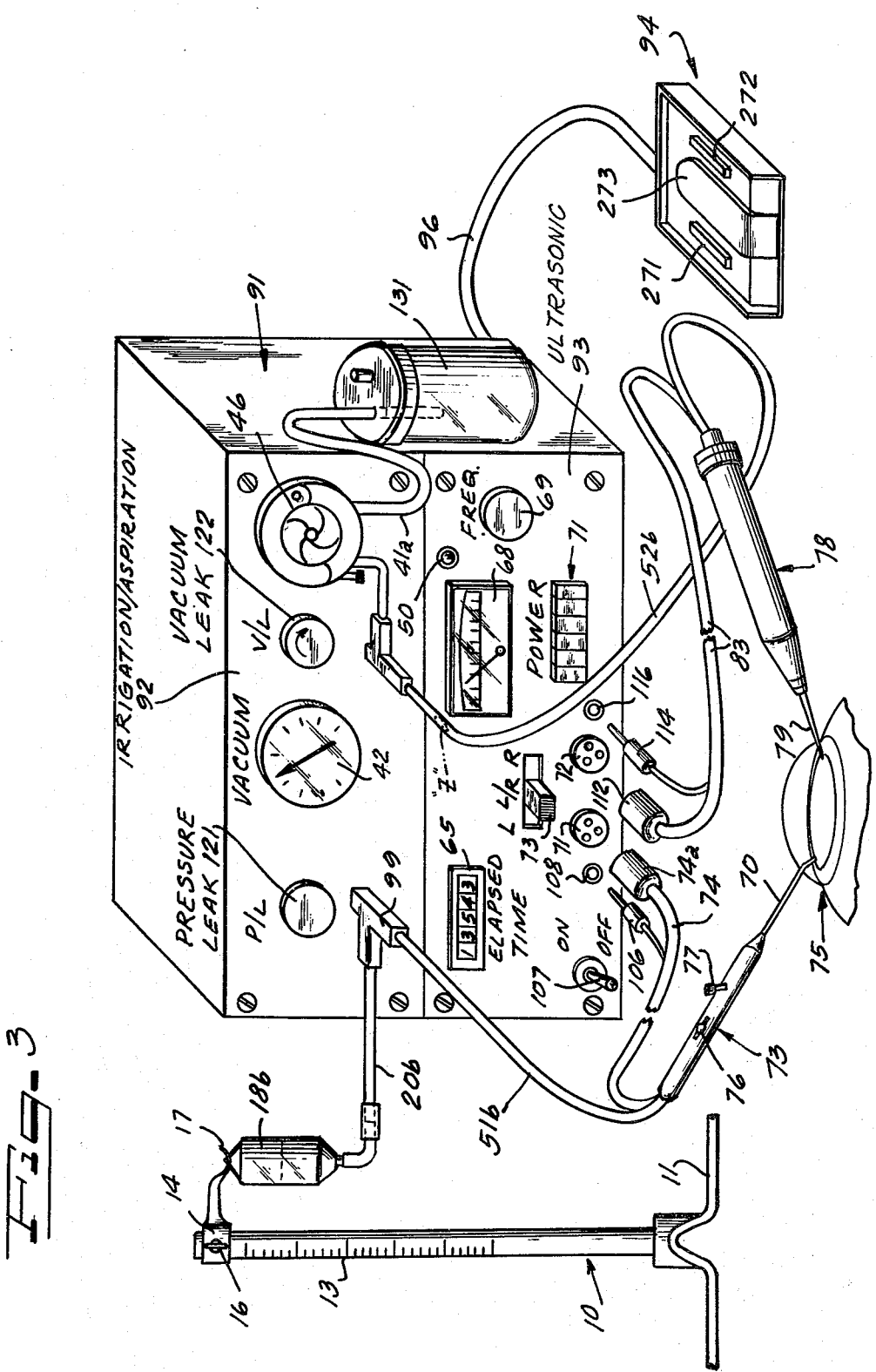

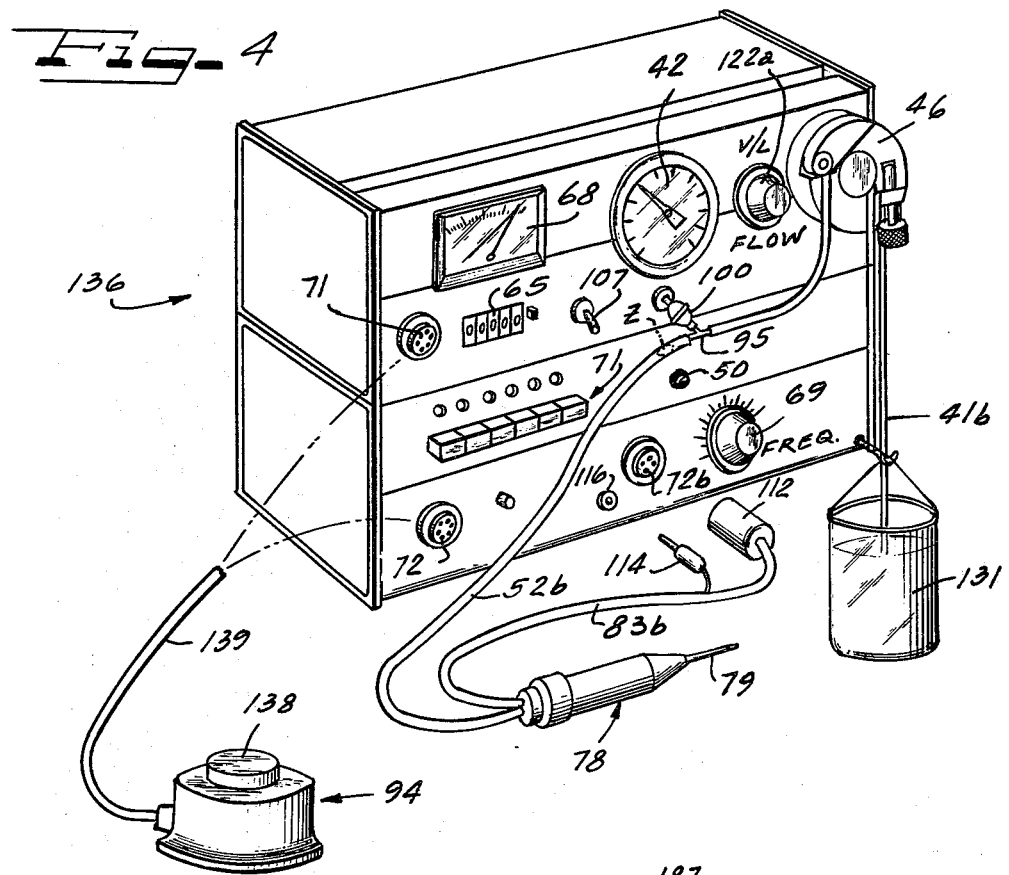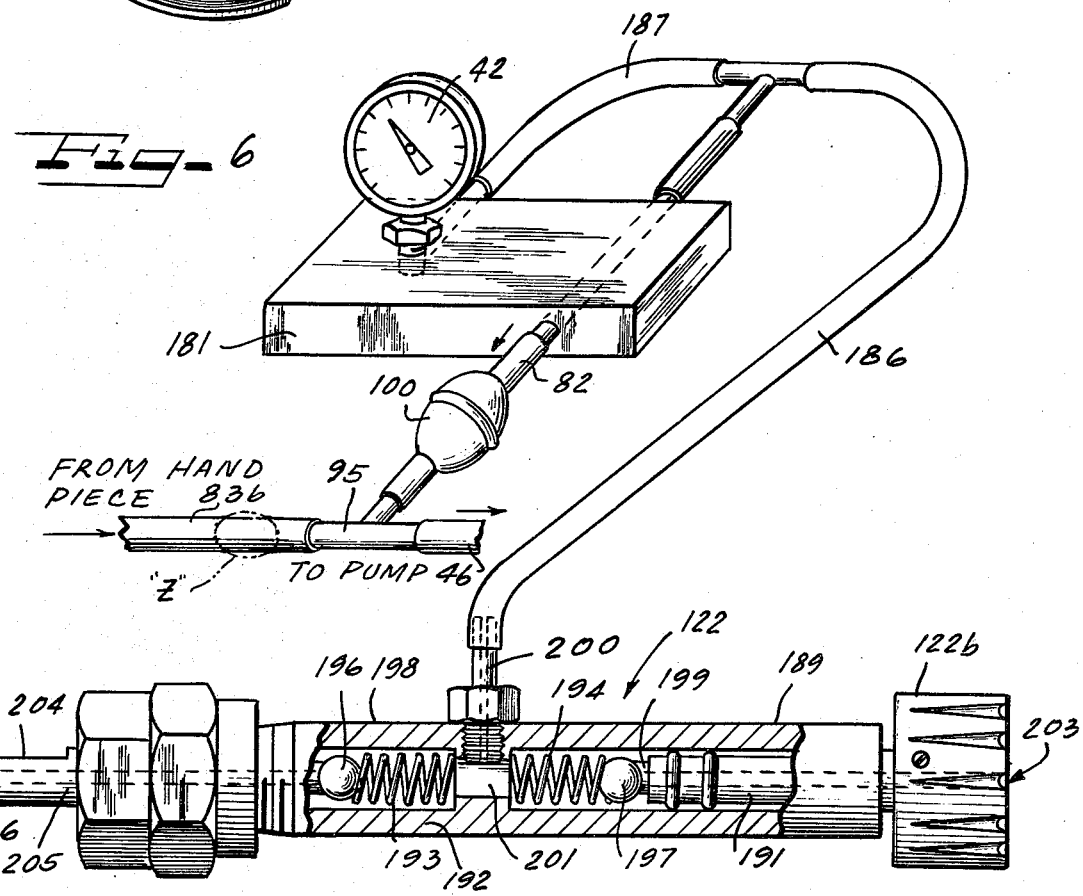

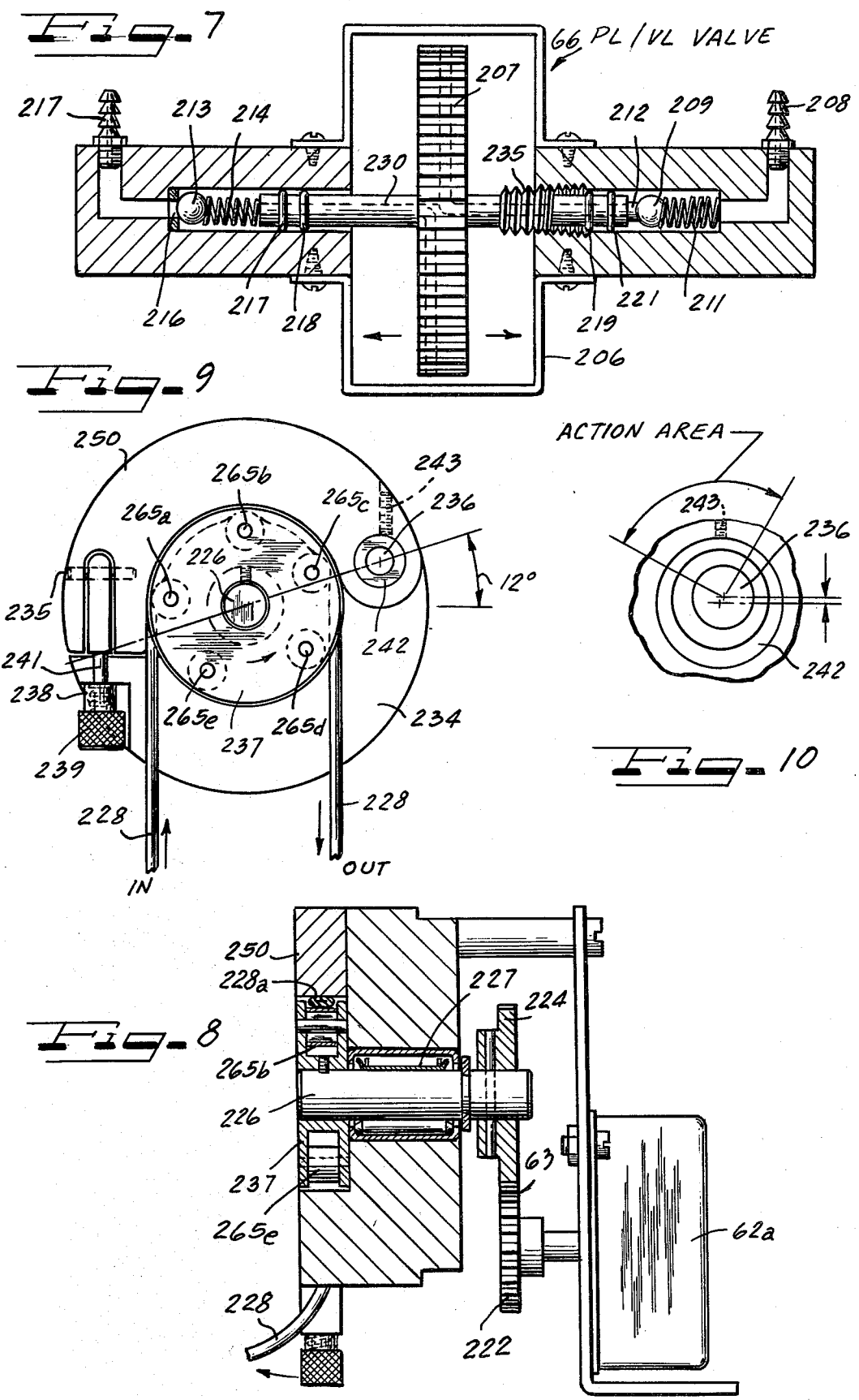

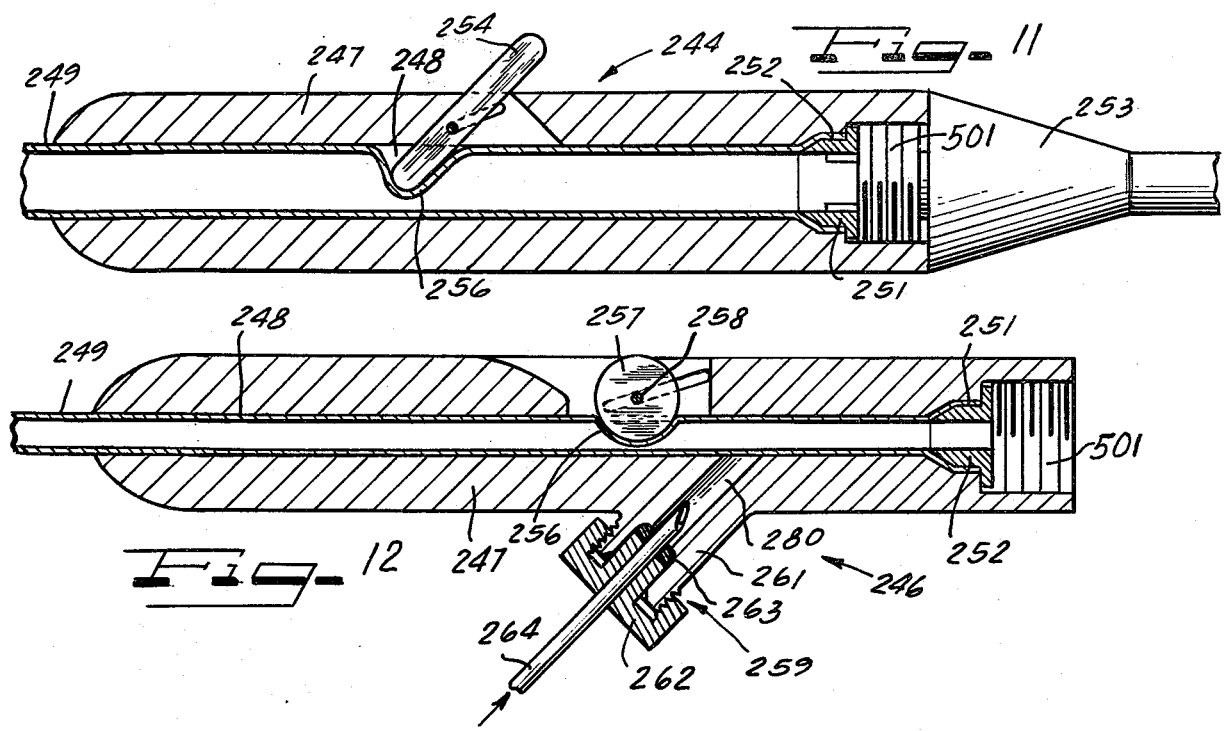
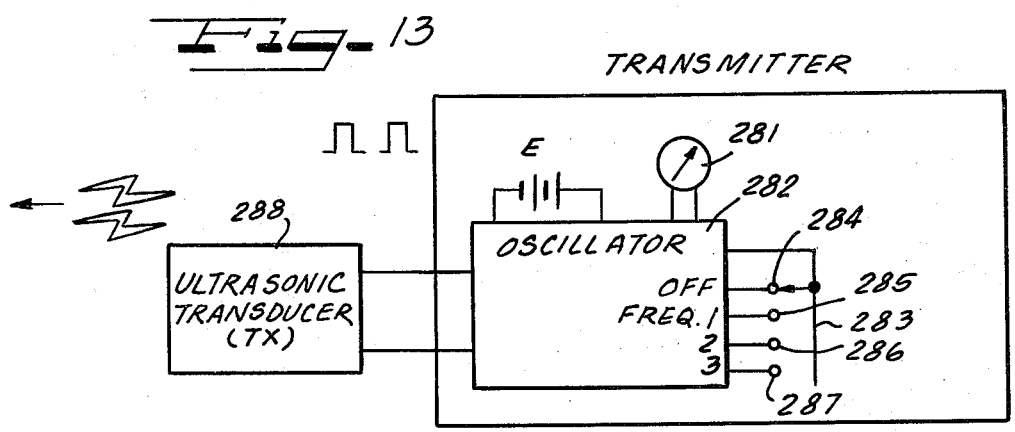
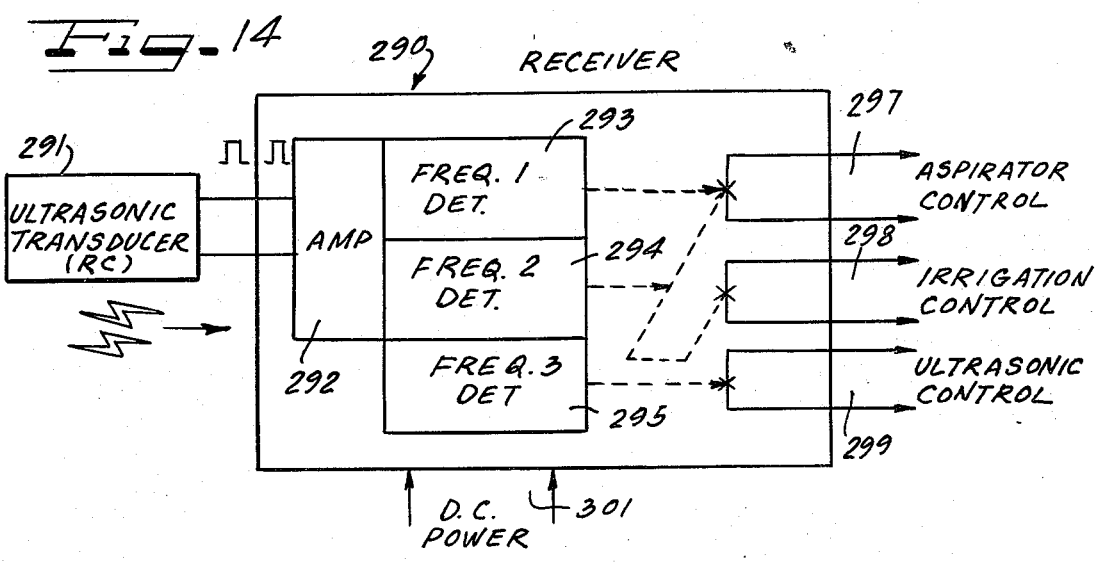

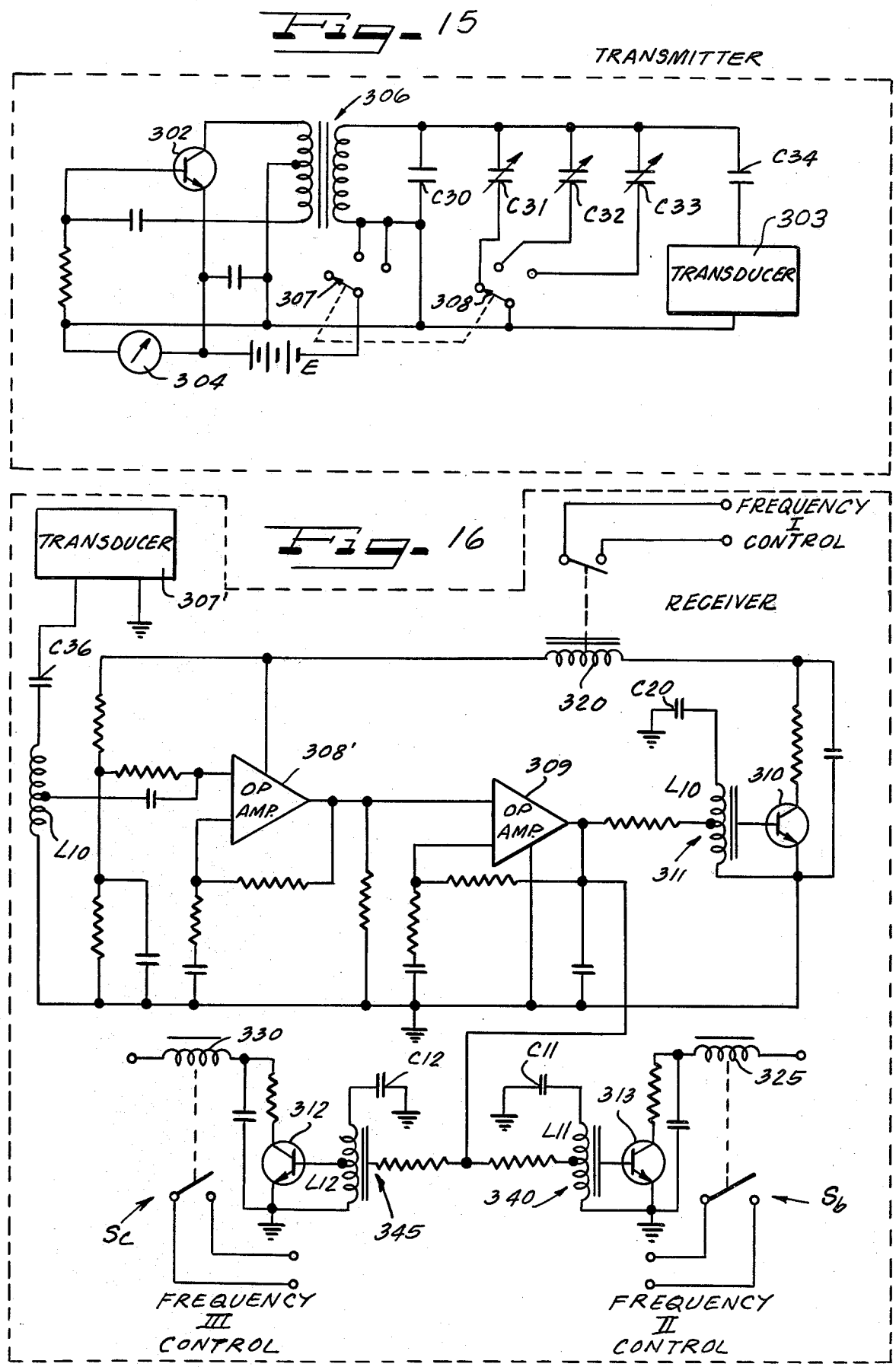

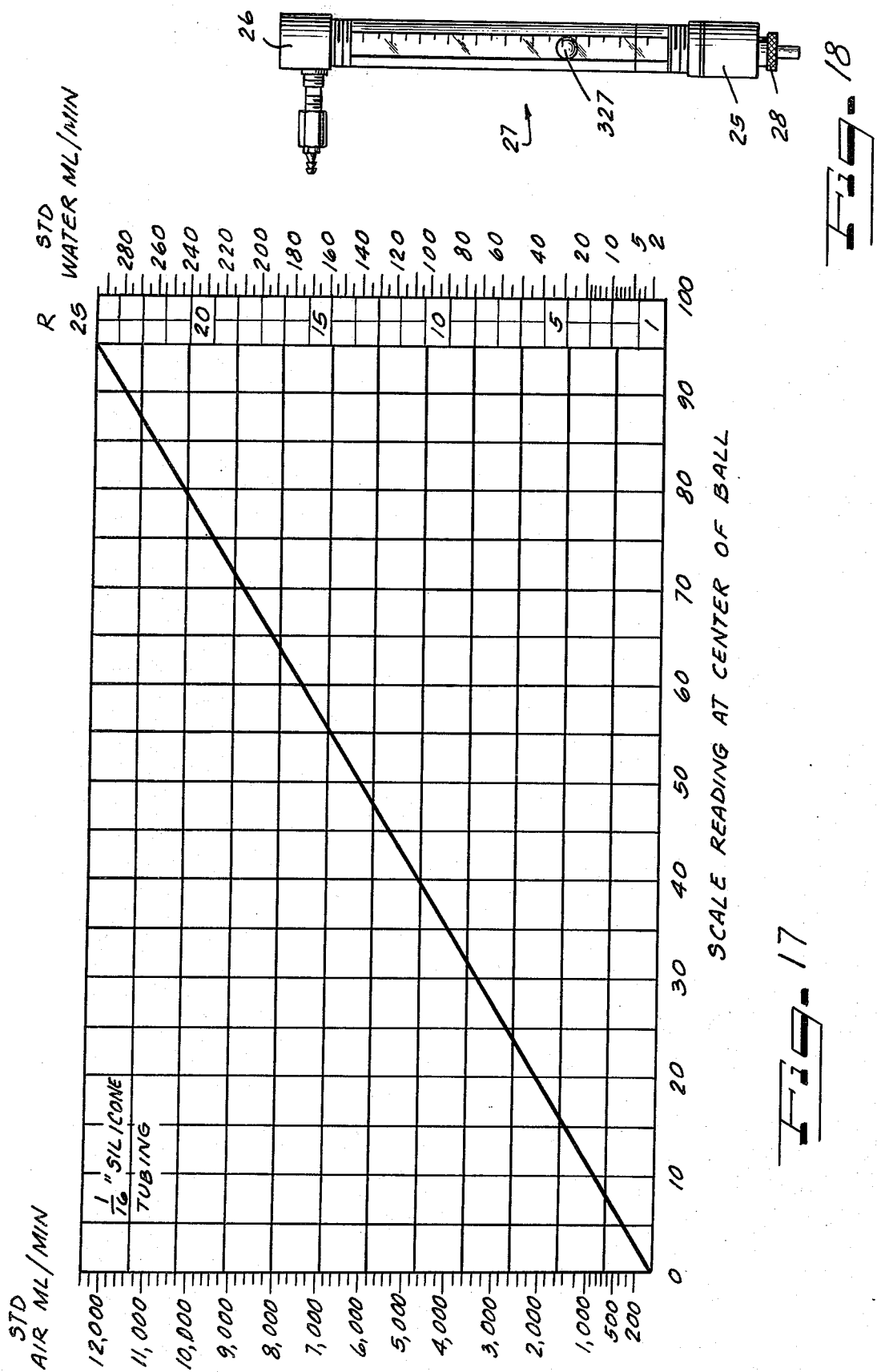

DEVICE AND METHOD FOR APPLYING PRECISE IRRIGATION, ASPIRATION, MEDICATION, ULTRASONIC POWER AND DWELL TIME TO BIOTISSUE FOR SURGERY AND TREATMENT

BACKGROUND OF THE INVENTION

1. Field of the Invention

This invention relates in general to a device and method for applying precise irrigation, aspiration, medication, ultrasonic power and dwell time to biotissue for surgery and treatment and in particular to an improvement on and in addition to the device disclosed in our U.S. Pat. No. 3,990,452 which issued on Nov. 9, 1976.

2. Description of the Prior Art

Substantial experience during operations in medical operating rooms using the ultrasonic equipment shown in our U.S. Pat. No. 3,990,452 which issued on Nov. 9, 1976 has disclosed that the needs of surgeons for providing proper operating room care to patients is far more complex and difficult than was a first realized by those supplying aspirating, irrigating and ultrasonic equipment. For example, prior art devices are on the market which includes complex aspirators and irrigators for removing fluids from body cavities such as the eye, lungs, veins, kidneys and other organs; yet, very few physical—as opposed to physiological—in situ, measurements have been made in these cavities such as the pressures and flow rates therein, and litte if any effort has been made to provide precise flow and pressure control when working in such body cavities.

This some situation exists for infusing medicine or treatment fluids to bathe (lavage) or flood tissue on a controlled basis at the invasion site as is required by the attendant doctors.

When ultrasound is additionally used there has been concern about the exposure of the tissue to the radiation and occasionally to its heating effect, yet few if any instruments in use today have been able to measure the true power in watts per unit of time, or in other words, the time rate of doing work applied to the tissue. The reason for this is not because this data is not necessary and required but due to the fact that the instrumentation has not been available heretofore to obtain or control this unique form of energy.

Another discovery was that the same equipment used for irrigation, aspiration and applying measured ultrasonic power to biological tissues frequently must also apply medication such as drugs or treatment fluids, for example, to the cavity or tissue being invaded in a manner similar to the heart-lung machine wherein the medicines are supplied to the machine rather than directly to the patient.

Our study has illustrated that a total consideration of the problem requires analysis of at least the following areas:

a. Irrigation
b. Aspiration
c. Medication
d. Power Control
e. Duration Control
f. Supplementary Devices For simplicity, it is assumed that the ultrasonic medical device described in our U.S. Pat. No. 3,990,452 will be used in the procedures described.

Definitions are where possible taken from Stedman's Medical Dictionary, 22 nd Edition.

A. Irrigation—(The washing out of a cavity or wound surface with a stream of fluid.)

The present art discloses bottles, flasks, retorts, tanks, etc., which are elevated or hanging, pressurized and so forth. All of these have one common feature for medical work and that is that they must contain sterile treatment or lavaging fluid so as to make it available to the attendants as needed. A great deal of ingenuity has gone into devising irrigation systems, some being very complex such as the closed cycle, blood circulatory system of the heart/lung machine; while others are as simple as a hanging I.V. bottle which has been used at least since 1902.

Some systems which use the hanging bottle are able to simultaneously create positive and negative pressure (vacuums) without the use of mechanical pumps by simply making use of the variation in atmospheric pressure over short elevational heights of several hanging bottles in a stepped series. Pumps and hand held syringes have also been used for irrigation purposes.

The inventors have discovered that the problem of irrigating tissue is basic and that you must meet several needs of the medical situation such as:

1. The system must be sterile and maintain its sterility which means it should not be open to the air, in other words, it must be a closed system.

2. It must provide irrigating fluid at whatever controllable pressure is needed.

3. It must provide whatever flow/volume rate is needed at that chosen pressure.

4. It must provide the fluids in the total volume and at the temperature needed by the patient as decided by the surgeon or technician present.

5. The system must be reliable so that it will not fail.

Additional to these absolute must-do features, the system should also desirably include the following features:

1. Be easy to clean to medical standards.
2. Be easy to set up and use.
3. Be reasonably priced, and
4. Be extremely reliable.

It is not always possible to accomplish all of the desirable features but the absolutely required features listed under 1 through 5 above must always be accomplished.

Our study has indicated that too many of the desirable features have been provided in irrigation systems while some of the absolutely required features have not been provided. For example, many devices are made of throw-away, one-time use, plastic which is the ultimate for cleaning; yet, these items can more easily be cleaned than replaced by the hospital and a great deal of supposedly sterile devices have been contaminated at delivery which is highly undesirable for the patient. On the other hand, many industrial production procedures in use today provide precisely heated, extremely uncontaminated fluids, at exactly required volumes and pressures to closed retorts or to processing reactors; yet, there is no known system of irrigation in use in the medical field which is as accurate as these industrial systems.

B. Aspiration—(Which is the removal by suction of air or fluid from a body cavity from a region where unusual collections have accumulated or from a container.)

As has been mentioned in our U.S. Pat. No. 3,990,452 the use of aspiration to remove fragmented dissolved or particulized biotissues is extremely old dating back to the Majima regime in Japan in A.D. 600. Aspiration or the removal of fluids from body cavities by use of an aspirator or the drawing or removing by suction can readily and without additional explanation be seen to be the application of a simple vacuum technique or more preferably and precisely the use of negative pressure to a tube, hose, needle, cannula, et al. Such negative pressure (vacuum) obviously has precise and exact limitations, ultimately reaching at its maximum 14.7 lbs/in$^2$ (1033.5 gms/cm$^2$) or converting to a more usable standard gauge, 33.9 feet of water (29.91 inches of Hg) at 0° C. and sea level.

There are many obvious methods for achieving relatively low pressure differentials or variations from the 29.9 inches of Hg standard pressure, down to the 0.1 inches of Hg required for use in medical work or in any usage of suction required for successful removal of fluids from the body cavities. Ultimately, however, since the limit of all methods are dependent from the atmospheric air pressure at sea level, they are in turn dependent upon the gravitational force; in other words gravity—applied to the air mass existing at the operating site of the aspirator—such pressure is therefore primarily a physical phenomenon of the terrestrial environment.

Generally, medical aspiration of body cavities can be accomplished with the so-called "low vacuum" range of low atmospheric negative-pressures, i.e., 14.7 lbs/in$^2$ (1033 gm/cm$^2$, or 10 torr) down to 1/76 th of an atmosphere, or 0.193 lbs/in$^2$ (13.59 gm/cm$^2$); in other words, $-750$ mm Hg ($-29.52''$ of Hg). (All pressures will be indicated in mm of Hg air pressure at 0° C. and sea level, and flow rates in ml/second—milliliters per second).

Since 1 torr = 1 mm of absolute pressure, a negative-pressure of 10 torr, "low vacuum", would equal $-750$ mm Hg ($-29.52''$ Hg) which can be readily obtained with most mechanical pumps of the piston, roller, diaphragm, vane, peristaltic types, and no vapor pumps are required.

Many types of mechanical pumps have been used for creating the negative-pressures used for evacuating body cavities, however, all of these do not have equal desirability for medical usages, as will be seen later.

C. Medication—(The act of medicating a medical substance or medicine to treat diseases by the giving of drugs; to impregnate with a medicinal substance.)

There are many widely scattered devices used for biotissue medication with the simplest, and most often used, being the standard medical syringe with a regular needle as its injector/applicator. Very little prior art exists for the simultaneous application of ultrasound and medication in the patented art.

In our invention, direct *sonification* is administered to the patient by way of the direct application of the tool of the invention into the tissue. In contrast, in heart-/lung machines, *medicine* is delivered to the machine and is then carried by the circulatory system of the machine to the patient, thus, confining its spread to that single path. This allows the doctor to use very strong medicines, and even materials which are not medicines, in the machine which then carries them into the patient under the severely constrained and positive strict control of the doctor. For example, dental drilling using ultrasound sometimes has used abrasive granules of boron carbide which after application is then removed since swallowing such material is not healthy or desirable. Another example exists in closed cycle anesthesia machines.

The present invention describes a unique closed system of flow control, feedback sensing and removal, which allows new usage of simultaneous injectable medicaments.

D. Power Control—(The control of the time rate of doing work which, since we use watts, is equal to 10$^7$ ergs/sec.)

Since in the use of ultrasound, a relatively unknown form of energy is applied to human tissues, it is very important that the total time-power, indicated in scientific units, be known. While the problem of determining the exact power going into the tissue is extremely difficult and in its early infancy, nevertheless, it is possible to accurately know the amount of power going into the ultrasonic applicator. Also, by using proportionality and substitution techniques, the time intensity exposure of the tissue to the radiation level being applied can be ascertained.

The prior art nowhere discusses the problem of measuring the true power in watts into the tissue at the application site.

In the present invention the correlation of a scientific watt, determined by a standard ampere method into a known resistance which has been developed by the inventors, allows more accurate calibrating and testing procedures for power control.

E. Duration Control—(The control and recording of the time of application of ultrasonic energy.)

The inventors use an elapsed time indicator which records in minutes and seconds the summation of the total time of application of ultrasonic energy which in turn is a measure of the total ultrasonic exposure time. Then the simple and single most important need is to accumulate the total time of application of the ultrasound as it is applied, to achieve the important intensity/dwell time factor. Thus, upon the application of three watts of ultrasound for 4 minutes—which constitutes 12 watt-minutes—we need to know if this has the same curative or traumatic effect as 6 watts of ultrasound applied for 2 minutes which also is equal to 12 watt-minutes? The inventors have also developed an operating hand piece which when used for surgery for example, can be flash autoclaved at 380° F. at 50 p.s.i.—an unusual accomplishment.

SUMMARY OF THE INVENTION

Three separate embodiments are disclosed, with the first being the preferred one, which comprises the latest and most comprehensive model; the second embodiment is our "transition" system while the third embodiment comprises the earlier developmental model.

The preferred embodiment will be primarily disclosed and the transition and earlier developmental models will more briefly be disclosed.

There are many places in medicine where the use of precisely controlled irrigation and aspiration along with proper provisions for medication and the applying of curative or surgical ultrasound is required. In the classic operation for the treatment of the pituitary gland through the nasal passage, it is necessary to use ultrasound with simultaneous irrigation and aspiration to provide this singular method of healing the diseased tissue. In the case of papillomatosis the application of ultrasound energy is the only known cure. In Meniere's disease, the application of ultrasonic energy is routinely provided and in several other medical areas ultrasound is creating speculative results of great and possible historical significant; as for example, in work on cancer.

The use of ultrasound for arterial cleanout, removal of blood clots and welding of bones are also of extreme interest. Ultransonic energy, when applied at various frequencies and intensities for different periods of time behaves quite differently. Thus, it has been known for years that ultrasound can coagulate or liquify blood. It can also agglomerate or disperse suspensions in industrial uses. It can heat materials or it can create molecular transpiration which drastically cools materials. Some of these phenomena are discussed in the following articles by the co-inventor Murry.

1. Ultrasonic Magazine, Vol. 1, No. 2, Fall, 1973.
2. Wire Technology, May 6, 1974.
3. ChemTech, February, April, May, 1975.

One must be extremely careful in applying ultrasonic energy to human beings and, thus, the present invention very carefully monitors and measures the application of ultrasonic energy at the time of application of such energy as well as accurately controls the pressures and quantities of both irrigating and aspirating fluids.

The present invention includes a preferred embodiment which has 5 modular sub-systems, which provide these features.

All systems for instrumenting and controlling a process must provide pipes, pumps, heaters, gauges, sensors, linkages, reservoirs, and so forth, as required to make the system work. The system of the present invention provides a source or sources of treatment fluids at known pressures and temperatures and at any selected flow rate required by the surgeon. It must be variable and controllable, preferably—in 1977—by some form of remote control. The inventors have discovered that the variable control presented a real problem and after trying many multiple switches on the floor, or in the handpiece, or operated by knee pressure, and so forth, it was discovered that the best control would be of a wireless form and, thus, the preferred embodiment uses a system similar to that used to remotely control a TV set. Thus, in an operating room it is desirable that all controls needed by the doctor be available without the use of wired connections.

*Area 1* in our system is the Control Area.

As mentioned, the need for controlling the flow rate and its pressure *into* the cavities under ultrasonic treatment or surgery is inherent in the irrigation problem. Different types of apparatuses were tried; the final one used a group of standard Gilmore pressure measurers and an input fluid control valve with a Cartesian diver vent-valve of excellent pressure control features. Thus, by the use of these standard available pressure/flow controls the input flow pressure and venting pressure can all be determined and controlled. Once these controls are set, they are relatively trouble free and very accurate. A second more practical embodiment uses the same principles of the first scientific embodiment but is decreased in size so as to provide a neat, clean, readily usable package at the irrigation input end and throughout the entire system.

With both of the embodiments mentioned above, it is possible to achieve any pressure from 0 to 150 mm of Hg and any flow rate from 0 to 500 ml/min, although it is necessary to change tubulation size to achieve all of the rates which might be demanded. FIG. 17 is a chart of the flow rate for one typical tubular material only, since the flow rate will vary with the internal resistance of the materials (i.e., the diameter). It is to be realized that in situ use of one of the embodiments, with full instrumentation available and regardless of what material is used, the operator can set his chosen flow rate at the desired pressure and it will stay there indefinitely. It is to noted that a very simple reference level should be, and is used, against which the venting valve acts. This reaction-control, once set, is stable at its setting, so if the doctor desires—for safety—a maximum pressure of 54 mm of pressure he sets his reaction-control at 54 mm and from then on his entire irrigation system will stay below 54 mm of Hg.

In the closed body cavity, as for example, the human or animal eye, the invention controls the pressure in the particular body cavity under treatment or surgery by paralleling that body cavity (the irrigation and aspiration chamber) with a "10×" or "Cyclopean" artificial eye, wherein all the sensing of the pressure in the interior or posterior chamber of the eye is separately accomplished. Since these two chambers are maintained in parallel at all times, the pressure will be the same in both the artificial "10×" eye as well as the actual body cavity. The efforts of prior systems to control the flow through the eye, so as to make its pressure constant, have been clumsy, dangerous and extremely difficult, and accurate control has not been accomplished. The use in the prior art of a single needle with two ducts, for irrigation and aspiration, which requires a three mm incision has prevented the accurate control obtained by the present invention. In the present invention, two separate ducts in two separate needles, solves the problem of collapse by preventing wide pressure variations.

The use of the "10×" or "Cyclopean" eye in parallel with the actual eye provides a large hydraulic cushion, which bypassing the actual eye, keeps it at whatever pressure it needs at all times as well as providing a constant reservoir of treatment fluid for the actual eye. If the aspirator tubing becomes plugged, then the bypass "10×" eye will keep the pressure across the eye chamber constant and safe in any event.

The "10×-Cyclopean" eye's (its actual chamber being in reality is mechanical closed chamber into which the bypass fluid flows and exits) allows the exact, innate pressure to be determined by the irrigation pressure, and the flow rate previously selected. The "10×" eye is similar to a typical, industrial processing chamber control. Mounted onto one end of the mechanical eye, is a unique group of diaphragms, stacked several deep, which are activated by the changing pressures in the "10×" eye. Mounted on these diaphragms in turn, are N-doped silicon strain gauges which give very large voltage outputs for the small pressure changes actually experienced. Since it is desired to maintain within close limits the pressure in this chamber, somewhere in the order of ±2 mm of Hg, the output of these strain gauges are used to control the speed of rotation of the aspirating pump-motor, so as to increase or decrease its speed by small amounts. Thus, since the motor is normally revolving at 300 rpm's, its plus or minus rpm variations are controlled and, thus, its ± variations in pumping rate. This can then be used to control the pressure in the artificial eye by a like ±2% or any other increment, e.g., ±10% or ±20 mm out of 100 mms (Hg), etc.

Once the input flow and pressure rate desired have been set, the aspirator negative-pressure is set to match it, which then "overrides" this gross setting, based on the minute changes in the artificial eye and in the actual eye. In operation, once the "Cyclop Control" is on, the variations of the pressure, as noticed by the raising and falling of the cornea (in the case of an eye cavity), is imperceptible.

Once the contaminated fluid leaves the eye (or other closed chamber) it is evacuated into a collecting bottle which is kept at the correct negative-pressure (vacuum) by the pre-selected speed control of the pump/motor. The vacuum level is very precisely held by the "Cyclop Control", but should the pressure become excessive, for any reason, a parallel mechanical safety "poppet-vent" is used, which can be set to unload at any desired preset pressure from zero to 380 mm of Hg (15″).

Note that the motor has a number of coupling, stepping ranges, providing 4 speeds to the pump spindle, any of which may be used to control the aspiration rate, and all of which will maintain these speeds once set, via our "Cyclop Control." This gross speed, 4-step, speed-control device is similar to that on a 4-speed phonograph turntable. Once the flow, liquid or air, leaves the collection bottle it goes through a unique peristaltic pump which will be described somewhat later, and from there goes into the recirculating feedback link. Note this is now a positive pressure (after the pump) and is applied as such to the closed cycle irrigation bottle, throttled down to the exact pressure requirements if need be. This closed circuit may be broken, if so desired, and operated at the pressure head of the hanging bottle alone.

Another of the most difficult problems which exists in the medical/surgical field is that of calcified or hard deposits of concretion. These are composed of salts of organic or inorganic acids (or of other material such as cholesterol). These form throughout the body anywhere and everywhere; from the deposits on teeth (dental calculi) to those in the pelvis (staghorn calculi) and elsewhere. Knowing these are hardened salts, it should be apparent that they are dissolvable by acids and, with the addition of simultaneous ultrasound, readily removed, . . . and such is the case.

The choice of the correct acids and/or other chemical agents required for each case of calculus deposits is complex, and must be ascertained by extensive and careful medical research, since the healthy tissue surrounding the calcified tissue will be readily attacked by any chemical which works on the calculus, because of its highly similar biological nature.

The inventive method of using two separate needles immediately provides a unique technique of infusory injection of the specific chemical into the calcified deposits while under the application of continuous, or bursts, of high intensity ultrasonic energy into a narrow confined region of the body and in precisely controlled amounts for a period of time determined specifically by the doctor.

Note, this again ties-in with the not too well known fact that chemical reactions; (1), speed to completion; (2), take place with far less use of the chemicals (e.g., a 4% solution of hydrochloric acid in the presence of 25 watts/cm of ultrasonic energy, is as effective, at least, as is 100% of the acid without ultrasound), and indeed, (3), takes place in seemingly impossible ways (e.g., mixing of mercury and water, or oil and water) with ultrasound present. For more on this, see the article of Murry in Chemical Technology, Vol. 5, February, April and June, 1975, for example.

To accomplish the injection into the body cavities under sonic surgery; "Sonurgy" (a neologism, by choice, which will be trademarked) with precise control, a "Y" tubulation configuration is inserted into the flow path of the irrigation system. The extra branch contains in it, a tiny spincture valve through which infusory micropipette injectors are inserted at the correct time in the operative scenario. By choice of the correct size of the metering micropipette, the specific amount of chemicals (or medicament) placed into the eye or tumor, for example, can be controlled.

Since one of the most intractable problems in cataract surgery has been that of brunescent or senile cataracts, this discovery and method of eliminating them, is of first importance to surgical intervention (i.e., intracapsular) in the removal of cataracts. However, it must be immediately added, that this controlled infusion of medicament is not limited to use for the removal only of hard cataracts, but can be applied with success to many other areas of surgery; for example, to the removal and/or treatment of joint deposits, including that of the spinal column.

Simple, straightforward injection of these chemicals into hardened deposits has been tried with some success, but the "plugging" of the cannula or needles used, hindered application. No such plugging takes place under the presence of the vibrating energy of controlled and simultaneously applied ultrasound, which not only facilitates penetration, but literally dissolved a path ahead of the needle as if by magic.

In addition to ease of high accelerating penetration, free of plugging, the vibrating needle creates intense microstreaming (as set forth in U.S. Pat. No. 3,990,452) vortices, which forces the medicament into the surrounding hard tissue in the manner of the ultrasonic "ink spitters", used in fast, electrostatic printing. Indeed, cell walls are penetrated without damage.

In addition to the need to provide irrigation pressure and flow control, sensitive pressure control and infusion—in the closed body cavity—and a collecting-/recirculating module, there is provided a precise power/time input indicator and a method of recording the total "dwell time" (i.e., that time during which the ultrasound is applied to the tissue) during which precise amounts of power are used.

Some information on such devices has been disclosed in our U.S. Pat. No. 3,990,452. During that earlier period the inventors developed these instruments as adjuncts, once the need became apparent, but since then, these units have been perfected and are now incorporated as standard items. These two devices provide, in turn, an Elapsed Time Meter and a Wattmeter, which later reads the true ultrasonic power going into the handpiece by integrating the voltage and current (at 40 kHz) as it is applied. In other words, application of the handpiece tool to tissue, once tuned to maximize its wattage input, reads the correct real power input fed to the handpiece. With this reading, and some minor calculations, one can tell, if not "how", at least, "how much" 40 kHz power is being applied to the invaded tissue. (Please note: since a great deal of the input power goes into the lavaging fluid and is carried away as heat, one cannot know how much really goes into the tissue, but only how much it is maximally exposed to.) Since every time the remote control, wireless foot switch turns on the ultrasound, the E.T.I (Elapsed Time Indicator) runs, and accumulates the time sequentially, we also know the total intensity/dwell factor for any one operation, i.e., the exposure of the invaded tissue to radiation for a measured period of time.

These main features disclose the invention in its interrelating complexity, which will be amplified hereinafter; however, certain other additional features of the invention will be disclosed, since they make this invention in combination with what is shown in our U.S. Pat. No. 3,990,452, a truly highly sophisticated medical device of unique scope and implication for the medical profession.

It has been the goal of the inventors to develop a method of putting the potentials of ultrasound into the services of medicine. This has been done, and shall be continued, and, it is to be understood that we did not, and do not, wish to merely make an "Eye Machine", an "Ear Machine", "Bone Machine", etc., but a universal, highly scientific reliable, effective ultrasonic energy device, which the vast majority of surgeons can use in their own specialties, with confidence, ease, and in the service of man. Therefore, we also disclose the following additions to our device.

There has been also added to this system a unique feature to the hitherto passive (ultrasonically speaking) irrigation needle, a quite small (in cross section) handpiece, about ⅜" in diameter, which may remain passive, be activated alone, or be activated in conjunction with the main operating probe during the irrigation/aspiration time. This device is of considerable use to the doctors in and during operations, usually working in conjunction with the other probe.

Other objects, features and advantages of the invention will be readily apparent from the following description of certain preferred embodiments thereof taken in conjunction with the accompanying drawings, although variations and modifications may be effected without departing from the spirit and scope of the novel concepts of the disclosure.

BRIEF DESCRIPTION OF THE DRAWINGS

FIG. 1 is an overall system view of the scientific flow system concept;

FIG. 2 is an overall view of the preferred practical embodiment;

FIG. 3 is an overall view of a transitional modification;

FIG. 4 illustrates another earlier modification/embodiment;

FIG. 6 illustrates an early model of a vacuum leak;

FIG. 7 is a drawing of an advanced model simultaneous pressure leak/vacuum leak, single valve system used in the preferred embodiment;

FIG. 8 is a sectional drawing of the unique peristaltic pump and motor anti-reversal system;

FIG. 9 is another view of the peristaltic pump showing rollers and spring lock;

FIG. 10 is another view of the offset and camming of the peristaltic pump;

FIG. 11 is a sectional drawing of a shutoff for the passive handpiece;

FIG. 12 is a sectional drawing of still another shutoff for the passive handpiece, with micro-pipette syringe injector part;

FIG. 13 is a block diagram of the transmitter part of the ultrasonic system for wireless control of the various subsystems;

FIG. 14 is a block diagram of the receiver part of the ultrasonic system for wireless control of the various subsystems;

FIG. 15 is a schematic drawing of the ultrasonic transmitter system;

FIG. 16 is a schematic drawing of the ultrasonic receiver system, showing control relays;

FIG. 17 is the flow rate chart for ⅜", silicon tubing at various readings of the valve settings of the flow meter; and, FIG. 18 is a view of a modified Gilmore type, pressure control valve used herein.

DESCRIPTION OF THE PREFERRED EMBODIMENTS

Figure 5:
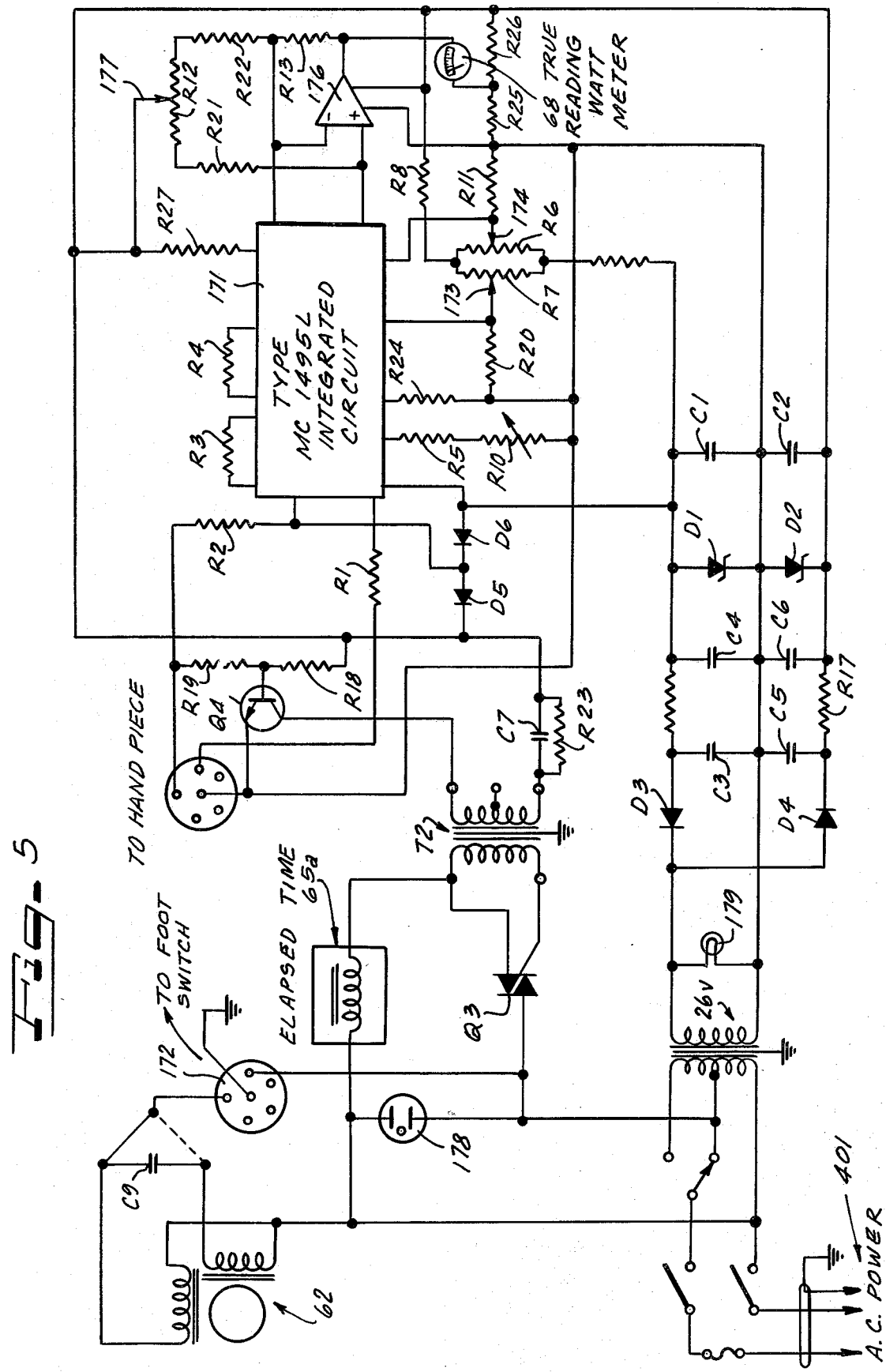
FIG. 5 is a complete operational diagram of the electronic circuit used in the independent aspiration/irrigation systems.

FIG. 1 is an overall view of the scientific configuration of the main features of the invention with certain subassembly portions of the invention put together so as to clarify the explanation of the main invention. The left portion of the drawing discloses the irrigation portion 34 and the right portion of the drawing relates to the aspiration portion 36. In the irrigation portion 34 a stand 10 has a base 11 and an upright member 12 which is provided with calibrations 13 which can be calibrated in both inches and metric units, thus, permitting whatever units are required to be used. A sliding clamp 14 can be locked with a set screw 16 and has a supporting hook 17 which supports a hanging bottle 18 that can be adjusted to any height by moving the clamp 14. A shut-off clamp 19 is placed below the bottle 18 on the supply tube 20. The bottle 18 may be adjusted in the relative range from 6 to 30 inches in height or up to 6 feet if it is used directly as a floor supported stand. The bottle 18 containing the treatment fluid may be 1, 2, 3 or more liters in capacity as required and is completely sealed from airborne contamination. Connected to the upright stand/bottle system is a length of tubing 20 made of silicon, polyethylene, teflon or other plastic as desired and of a suitable length. The tubing 20 is connected to a flow meter/flow control 21 which may be a modified Gilmore flow unit type 390 capable of indicating and controlling the flow of the treatment fluid from 0 to 200 ml/minute. The specific flow rate required is controlled by the micrometric tapered choking control valve 22 which can be manually adjusted. The effect of the choking control valve 22 can be observed on the flow indicator 21 which is the standard Bernoulli rising-ball type indicator. Our research has determined that extremely small variations in flow rates for any given size of tubing and input pressures, and for all feasible treatment fluids having poise ratings of (3–12) C.P. viscosity, can use a standardized indicator ball to indicate the time-flow rate. If the treatment fluids used are more or less of the same viscosity, as measured by a separate indicator, a ball can be selected of the proper density to suit our needs once the viscosity of the fluid has been measured by a counter-poise gauge.

The flowmeter/flow control valve indicator 21 is tubular connected by fittings 23 and plastic tubing 24, of the same I.D. and pastic material as selected for tube 20, to a pressure control/gauge 27. We have found that this gauge 27 must be modified so as to operate within the range of the treatment fluids used and not with the standard mercury usually supplied, since it is connected to a fluid source and not to a gas source. FIG. 18 illustrates the modified Gilmore gauge 27 and includes the ball 327.

Portion 26 of the gauge 27 is a modified pressure head check valve and lower portion 25 is the bottom fluid reservoir; while the knob 28 is the pressure control adjustment which can be varied to change the pressure from 0 to 200 mm of Hg (or, since generally a fluid close to the density of water is used in medical fields, from 0–2720 mm of H₂O). By adjusting, the flow indicator 21 by varying its control valve 22 and the pressure control gauge 27, by adjusting the knob 28, the flow rate can be established at any rate desired, at any pressure desired. This is novel in the medical irrigation field and gives results which are very advantageous.

An output supply tube 31 supplies the irrigation medicating and treatment fluid to a Cartesian Diver type pressure safety control 29. The principle of the Cartesian Diver control is well known in physics and the Diver 30 can be controlled by adjusting the knob 32 so as to prescribe an upper limit to the pressure which is available. It is to be noted that the Diver as used herein is in a modified form as a pressure-leak instead of the usual vacuum-leak configuration.

FIG. 17 comprises a chart which shows the overall calibration of the irrigation part of the system illustrated at the left in the dotted line portion on FIG. 1. It is to be observed that for a given size of tubing inside diameter, the flow rate and pressure change can be controlled by the two controls 21 and 27. Pressure safety control 29 does not become a part of the system until the pressure exceeds the safety level preset into it, at which time all that the control settings established by knob 22 and knob 28 can do, is to adjust the pressure downwardly and never upwardly above the level set by the safety level knob 32, which provides a very desirable safety feature.

The aspiration portion 36 of the system illustrated in FIG. 1 shown to the right of the 2nd dotted line in FIG. 1 provides the vacuum negative-pressure suction and operates with a standard Cartesian Diver safety valve 37 that has an adjustable control knob 38. By varying the control knob 38, the upper safe limit of the vacuum suction can be established at any desired figure from 0 to −381 mm Hg (0 to −15" of Hg or 0 to −½ of an atmosphere). In normal use, Diver 29 and Diver 37 will be closely set to each others range since it is known that the input pressure and the output vacuum-suction pressure should be at the exact differential needed to maintain the flow rate required without collapsing the chamber in which a medical operation or other intervention activity is occurring. It is to be noted that in this application it is gauge pressure, not the absolute pressure being defined, since the entire system including the controlled cavity 48, which may be a biological cavity, which is exposed to normal atmospheric pressure; in other words, 14.7 p.s.i.

Another tube 55 is connected from safety valve 37 to a standard two hole vacuum bottle 39 which has its upper end sealed. The treatment fluid and microdebrided material from the biological cavity may then be collected in the bottle 39. A tube 41 extends from bottle 39 to a tee connector which has a vacuum gauge 42 connected to its branch and which might read range from 0 to −10" (or 0 to −254 mm) while the upstream output 44 of the tee 43 is connected to a larger size of tubing 44 which is passed through the peristaltic pump 46 which provides the suction for the system. The still further downstream tube 47 at the output of the pump will have a positive pressure equivalent to the negative pressure in tube 44 before the pump 46. The tube 47 is fed back to the hanging bottle 18 and thus a closed sterile system is provided. It is to be noted that it is gas pressure downstream not liquid pressure and no post-passage contamination of the sterile treatment fluid in the hanging bottle 18 is possible.

In FIG. 1, a simulated biological test chamber 48 is illustrated and one of the main features of the invention is that an artificial cavity 49 of 10 times the size of the artificial or biological cavity 48 is placed in parallel with the test cavity 48 or a biological cavity and these cavities are interconnected by tubes 51 and 52 as shown. In this invention, particularly in the case of eye work, and in this arrangement we designate the 10× cavity 49 as a Cyclops eye, for obvious reasons. The large cavity 49 sees or experiences simultaneously the same pressure variations that the anterior chamber of the eye or other body cavity does, minus some very slight pressure losses. If the pressure in a biological chamber 48 raises or lowers plus or minus an amount of 10%—usually 1%—the 10× chamber 49 also experiences a similar pressure increase or decrease and sensing diaphragms 57 mounted in a housing 56 distend or contract accordingly since the stacked diaphragms are exposed to this pressure variation. It is to be realized, of course, that input tube 53 is connected to the chambers 48 and 49 and output tube 54 extends from the pressure control 37 to the chambers 48 and 49.

The diaphragm 57 is enclosed in a sealed chamber 56 which can be opened to atmosphere (or in the case of an anterior chamber of the eye to the same ambience) or to positive or negative pressures as desired and the diaphragm can be set to respond to any range or pressure operations desired. Generally, the exterior surface of diaphragm 57 will be subjected to atmospheric pressure.

Attached and firmly bonded to diaphragm 57, or connected to it, is a pressure-to-voltage transducer 58 which may consist of N-doped silicon formed into a strain gauge, or alternatively, may consist of a linear potentiometer. The transducer 58 functions to convert minute variations in the distention or contraction of the diaphragm-bellows 57, caused by pressure variations, into voltages which are fed to a voltage controlled oscillator/amplifier 61 through lead 59 which provides fine speed control for the motor which drives the peristaltic pump 46.

A motor 62 receives the output of the oscillator/amplifier 61 and the motor 62 may be a Molor type 12 pole 60 cps motor which normally rotates at 300 RPM. When it receives from amplifier 61, 54 to 66 cycle current the speed of the motor will vary from 280 to 330 RPM or plus or minus 10% around its normal means speed of 300 RPM. This will produce a pronounced effect on the delivery rate of peristaltic pump 46 to which it is connected by fixed gearing 63 and shafting 226 as shown in FIG. 8.

Thus, FIG. 1 illustrates the basic operational concept of the invention which is designed to provide any irrigation flow rate, at any pressure, into a finite biological chamber, along with controlled evacuation rates of aspiration while maintaining the chambers patency within small limits; meanwhile rigidly providing for complete safety of the patient.

FIG. 2 is a practical embodiment of the apparatus illustrated in FIG. 1 and those parts which are commonly numbered in FIG. 2 correspond to those having the same numbers in FIG. 1. The stand 10 supports the calibrated rod 13 in a three footed base 11 and the rod 13 is calibrated in inches of pressure arbitrarily since the pressure gauge 27 is calibrated in inches of mercury. The clamp 14 is locked in place by set screw 16 and supports the flask 18 containing the treatment fluid and the clamp 19 controls the primary on-off flow of the treatment fluid. Feedback pressure is supplied by the pump 46 through tubing 47 which is connected to the hanging flask 18 by a suitable fitting. The input flow pressure available is again monitored and set by knob 28 on gauge 27 and the flow is controlled by built-in metering valve 22. The housing 60 of the machine illustrated in FIG. 2 contains many of the internal connections which correspond to those illustrated in FIG. 1. The fluid from the hanging bottle 18 passes through the tube 20 into the case 60 and emerges from fitting 81 which is connectible to tubing 51a of handpiece 73 which has a needle 70 that can be inserted into a suitable chamber such as an eye 75. The handpiece 78 has an aspirating needle 79 which can be inserted into the eye and a tubing 52a is connectible to a fitting 82 which is internally connected to a tube 55 which is connected as shown in the drawings to the collecting flask 39a. Flask 39a is exhausted to a desired vacuum negative-pressure as indicated on gauge 42, which is also internally connected by a suitable tube not shown from the tube 41 to the gauge 42 at "X". The tubing 41 is connected to tubing 44 and internally to dual pressure leak/vacuum leak 66 which will be described later. The pump 46 provides pressure in tubing 47 which is used to repressurize hanging bottle 18 through the tubing 47. The 10× artificial chamber 49, the sensory diaphragm 57 with its housing and the pressure sensor 58 and the voltage-to-frequency converter 61, as well as the low RPM drive motor 62 and the four-step speed changer 63 are all mounted inside the case 60. The speed-change lever 65 is connected to the speed changer 63 and extends from the case as shown to allow the major speed ranges to be adjusted.

Certain items which are shown in detail in U.S. Pat. No. 3,990,452 are also mounted in the case 60. These are the true reading wattmeter 68. A knob 69 controls the frequency of the ultrasonic oscillator as set forth in U.S. Pat. No. 3,990,452 and its correct tuning is indicated by the dimming of amber light 50 and the peaking of the wattmeter 68. The level of power desired is of course selected by the push-button system 71 while the elapsed cumulative time of application of the ultrasound is continuously recorded on elasped time indicator 65.

The preferred and practical embodiment illustrated in FIG. 2 shows a new feature of great use; the dual ultrasonic output available at terminals 71 and 72, marked L and R, and controlled by switch 73. The switch 73 is a three way switch permitting sonic energy to be available at jacks 71 and/or 72. Handpiece 73 is shown with a bent irrigation needle supplying fluid from the hanging bottle 18 but it may be replaced by simply a straight irrigating needle or a "butterfly" needle and may not furnish ultrasound if so desired. If ultrasound is to be supplied, the ultrasound supply cord 74 is provided with a suitable plug for inserting into output socket 71. In the configuration shown handpiece 73 may be provided ultrasound energy from socket 71 and irrigating fluid from tubulation fitting 81. This handpiece further includes a spincture valve 77—shown elsewhere in FIG. 12—which is normally closed but which is available for inserting micropipettes for injecting or infusing special fluids such as needed for dissolving stones, deposits or cataracts. A slide valve 76 provides control of the treatment fluid applied to the needle 70. The needle 70 may be in a variety of shapes and gauges for different types of operations and purposes.

The second handpiece 78 is of the form illustrated in U.S. Pat. No. 3,990,452 and has an instrument 79 affixed such as the tip illustrated and receives ultrasound through the cable 83 which may be inserted into the socket 72 and is provided with an aspirating tube 52a which is connected to the aspirating fitting 82 of the machine 60 so as to provide aspirated fluid to the bottle 39a.

A pressure-leak/vacuum-leak control (PL/VL valve) 66 comprises a new feature of this invention and will be described in detail later. For control of the machine and its many features, a wireless remote control switch 86 provides control without wires to the machine 60 for controlling the machine during the course of an operation. It will be described in greater detail subsequently.

FIG. 3 illustrates an earlier modification of the invention which was in a simpler form and the machine 91 is formed in two portions, an irrigation/aspiration portion 92 and an ultrasonic portion 93. Many of the parts are common to those illustrated in FIGS. 1 and 2 and the hanging bottle 18b supplies fluid through a tube 20b and a tee connector 99 to tube 51b for providing irrigating fluid to the needle 70 of the handpiece 73. A separated vacuum leak 122(V/L) and a pressure leak 121(P/L) in combination, work similar to the pressure-leak/vacuum-leak 66 illustrated in FIG. 2, except each valve 121 and 122 must be separately set, but once set controls the positive and negative-pressure (vacuum) available. The foot switch 94 operates similar to the wireless control 86 which is, however, a remote R.F. transmitter, while in the model illustrated in FIG. 3 a cable 96 hard-wire connects the control 94 to the machine 91. The control 94 controls: (1), 271 irrigation; (2), 272 aspiration; and (3), 273 ultrasound. Ultrasound can be available either alone, at one of the two handpieces 73 or 78, or at both simultaneously as determined by the setting of switch 73. Ultrasound is applied to the handpiece 73 through cable 74 and plug 74a which can be inserted into socket 71. A redundant grounding plug 106 can be inserted into socket 108. Ultrasound for the handpiece 78 can be supplied through cable 83 and plug 112 which can be inserted into socket 72 and grounding plug 114 can be connected into redundant grounding socket 116.

FIG. 4 illustrates a still earlier modified embodiment wherein the machine 136 included many elements common from the system disclosed in U.S. Pat. No. 3,990,452 including a single aspirating handpiece 78 with a needle 79 and an ultrasound supply plug 112 and grounding plug 114 receivable in sockets 72 and 116 respectively to supply ultrasound to the handpiece 78. A frequency control knob 69 allowed the frequency of the ultrasonic generator to be adjusted while an aspirating tube 52b is connected from the handpiece to a peristaltic pump 46 which provides an output through tube 41b to the fluid collecting bottle 131. A wattmeter 68 and an elapsed time meter 65 are provided. A simple V/L vacuum leak 122a is provided as is a large vacuum gauge 42 for measuring the degree of vacuum in the aspirating line 52b while the power selector switches 71 and dimming amber light 50 indicates the selected power level is at peak. The peristaltic pump 46 provides the aspirating evacuation for the handpiece 78 while the microdebrided material is collected in collector flask 131 which might be a plastic bag. A 5 to 8 micron replaceable filter 100 is placed between the tee connecting joint 95 and the gauge/vacuum leak 42 and 122a to prevent debris from contaminating or plugging these components.

Thus, the apparatus illustrated in FIGS. 1 through 4 comprises various modifications of machines which have been reduced to practice and used, as for example, in cataract operations.

In our U.S. Pat. No. 3,990,452, FIG. 12 thereat, is illustrated a wattmeter 107 and the elapsed time indicator 108. FIG. 10 of that patent illustrated the internal connections, including the ultrasonic generator, to the handpiece.

FIG. 5 hereat illustrates the new added circuit using a type MC1495L integrated circuit 171 which together with integrated circuit 176 generates an output voltage $V_{out}$, which equals $KV_1V_2$, which causes operation of our true reading wattmeter 68.

"K" above, is a gain factor which is set for the proper range calibration of the meter. The voltage which is applied to integrated circuit 171 at the junction between resistor R1 and the integrated circuit is derived from the voltage which appears across the handpiece 78 (the microdebrider probe). The voltage $V_2$ is a voltage derived from the load current into the handpiece 78. Since these are at all times in proper phase, voltage times current is equal to watts and the power measurement is indicated on the meter 68.

The elapsed time indicator 65a is a synchronous Veeder-Root type multiple-disc counter driven by a 60 cycle clock motor (not shown). In order to operate this device so as to make it indicate when ultrasonic energy is being applied to the biotissue, it is necessary to apply 60 cycle, 120 volt power to the Timer's motor, coincidence with operation of the foot switch 94 which has in it two spring-loaded make-contacts. In the partially depressed position switch 94 turns on the pump 46 causing suction to appear. Fully depressing switch 94 to its bottom position, causes the ultrasonic generator to produce 40 kHz energy. A portion of this is picked off and amplified by transistor Q4 in FIG. 5 and this output is then coupled through transformer T2 and supplied to a triac Q3 which acts as a switch to turn on the timer 65a. In this manner only, and positively, when ultrasound is generated is time logged on this accumulating meter which is necessary and desirable as pointed out previously. Thus, a simple need to turn "on" and "off" AC 60 cycle power has been refined to directly record the time/dwell factor of the ultrasonic energy which is present.

The double vacuum-leak/safety device illustrated in the embodiment of FIG. 4 is shown in detail in FIG. 6. The pump 46 in FIG. 4 can pump to a negative pressure of −15 inches (−381 mm) of Hg which is far too much for use in many parts of the human body, especially the human eye. Hence, it is necessary to provide safety factors at every step of the procedure. By utilizing the proper thickness of tubing wall in the internal interconnecting tubing for example—one which will collapse and close off the pumping at a negative pressure—an upper limit of −15 inches of Hg can be obtained for example.

FIG. 6 illustrates a distribution block 181 which is a solid drilled-out piece of brass connected internally so as to interconnect the gauge 42, the suction output 82, the hose 186 & 187 which collapses at a −15 inches of Hg and the double vacuum-leak 122. When negative pressure is applied by the pump 46 to the tubulation of the system and the feed tube from the handpiece is pinched-off at "Z" on the tube 52b which goes to the handpiece 78, the gauge 42 will read the full head negative-pressure of the pump 46 which is normally about −29.92 inches of Hg. However, this will only be allowed to reach −15 inches of Hg due to the collapse of the tube 82 at −15 inches and then only if vacuum leaks 198 and 189 are screwed completely in.

Further break points are set in by adjusting the leak-valve 189 and 198 which consists of a body of hard plastic 192 and a pair of safety springs 193 and 194, two ball bearings 196 and 197 and a pair of stems 191 and 205. O-ring seals are used on each stem to seal off the stem so air can only enter the inner chamber 201 through the leak holes 206 and 203. In operation, the front valve 198 is closed down completely by means of an external knob(not shown), but which is the same as knob 122b shown for valve 189. When valve 198 is completely closed, a pinching off pressure is applied at "Z" on the tubing 83b coming from handpiece 78. Then high limit valve 189 is adjusted with knob 122b until the vacuum gauge 42 reaches the desired upper-set limit usually −10 inches of Hg. Since this adjustment is inside the case 136 and sealed at the factory the negative-vacuum pressure will never exceed −10 inches of Hg since any suction on fitting 200 will appear in the chamber 201 and cause the ball 197 to unseat at −10 inches of negative pressure, thus, allowing air to leak into chamber 201 through the leak hole 203.

Once this is set and sealed internally, the front panel knob connected to shaft 204 must be adjusted in a like manner to the operating pre-set negative-pressure desired, usually −3 to −5 inches of Hg (−76.2 to −127 mm of Hg). This is varied as needed during the course of the operation and the doctor can obtain zero to a maximum of −10 inches of Hg via this control.

In the embodiment illustrated in FIG. 3, two leak valves similar in operation to that illustrated in FIG. 6 are used, however, one valve is a pressure-breaker valve or a "pressure leak". The principle of the pressure leak/vacuum leak valve is illustrated in FIG. 7.

The right side of the apparatus in FIG. 7 comprises the vacuum valve illustrated in FIG. 6 and operates as previously described. In this valve, however, only a single knob 207 is used which operates so as to simultaneously control the low levels of vacuum and pressure required. By rotating the thumb wheel knob 207 so that it moves to the right, we increase the amount of negative pressure required to make the ball 209 move from its seat 212 while at the same time lowering the amount of input pressure required to move the ball 213 off of its seat 216. It is to be noted that rotation of the knob 207 causes the shaft 230 to move relative to the housing 206 due to the threads 235 which accomplish this result. Thus, a differential action of great sensitivity at the lower ranges of pressure and vacuum are obtained which are necessary in biological work.

Thus, the doubleacting valve 66 may be placed across the artificial 10× X cavity or chamber and its diaphragm can then be delicately set to the zero level or other level required. This same valve can also be used for different pressure ranges and/or vacuum ranges by simply changing springs 214 and 211 as needed and the ranges of the two valves need not be the same.

The unique floating peristaltic pump 46 is illustrated in FIGS. 8, 9 and 10. In FIG. 8, the motor 62a has an output shaft which is connected to a nylon gear 222 which is connected by toothed engagement 63 to nylon gear 224 which drives the peristaltic pump shaft 226. The motor 62a may be a 12 pole magneto-ceramic core motor which turns synchronously at 300 RPM if 60 cycle power is applied. Since the speed is low, it is possible to use a single pair of nylon gears to reduce the RPM to that required for the flow rates of 25 ml to 200 ml per minute with great ease and efficiency. By utilizing a large diameter shaft 226, a high concentricity is obtained with anti-reverse bearing 227 while excellent clutching action is obtained. Bearing 227 is a dual acting rolling-pin bearing with a built-in no-reverse clutching action which is required so that no possible reversing of the motor can take place, thus absolutely preventing return of all debrided material back into the eye or other body cavity. The bearing used is a standard Torrington type DC thin-cup, roller-clutch bearing and is highly effective. Thus, the advantages of low RPM is obtained with a few gears as is a positive no-reverse feature not previously available.

A major breakthrough in a peristaltic pump design has been accomplished in the present invention and is one of great importance because we have discovered that the major disadvantages of peristaltic pumps of the prior art is that of the head spacing. In other words, if the spacing between the rotor 237 and the clamping head 250 is too small the peristaltic pump acts as a perfect shoe-type brake, overheating the motor and seriously wasting motor power; while, if the spacing is too great, the pump will not pump at all or pump only slowly, intermittently and inadequately.

We have discovered that by rotating the head 250 to an offset angle of 12° relative to the rotor center, as illustrated in FIG. 9 and by using a camming action at pivot point 236 that the head spacing can be uniquely adjusted—over the proscribed action area—of plus or minus 0.010 inches, thus, providing an adjustment for any variations in tubing size which heretofore can be a constant cause of trouble. Furthermore, an additional springing action is applied at 238 by the adjustment of a knob 239. A swivel joint 235 is provided for opening while 238 contains a spring around its enclosed shaft 241. The spacing between the head 250 and the rotor 237 can be accomplished by adjusting the cam 242 which is an eccentric cam. This cam 242 should be adjusted with the spring 238 uncompressed by turning the knob 239 until no pumping occurs with the tubing 228 in place in the pump. Set screw 243 is then locked down to hold the eccentric cam 242 in position, then the knob 239 may be rotated to tighten the spring 238 so as to increase the pressure on the tubing gradually as the shaft 226 rotates. It will be observed that the pump will begin to take hold and the vacuum gauge needle will begin to bounce which will occur at a relatively low reading and frequency. Further turning of the knob 239 will cause the gauge's bouncing to gradually decrease and the gauge will begin a steady climb to a higher negative pressure; in other words, vacuum level. Putting slightly more pressure on the spring by turning the knob 239 still further and all bounciness of the gauge needle will completely disappear and a clean steady climb and negative-pressure will be achieved. One additional slight adjustment of about one-quarter turn and the gauge will be precisely set and the pump will be pumping evenly and solidly with a slight reserve pressure on it.

Observation of this action with the tubing in place will show that the spring 238 is causing the swing-head 250 to bounce upward and downward continuously as the rotor 237 is turning and the tubing is being alternately compressed by the five rollers 265a through e. The pulsating action is very smooth and no braking action exists. Furthermore, any solid debris coming into the tubing acts against the compression of spring 238 and passes easily through the pump. The secret of the success of the pump is in the 12° offset and the "bouncy" spring 238. The pump is silent and smooth operating at all speeds and is practically failure proof.

The handpiece 73 illustrated in FIG. 3 provides a new approach to irrigation and is generally used with a two needle technique of simultaneously but separate irrigation/aspiration and has great advantages over the one needle, two duct, technique of the prior art. Two needles have great advantages particularly when working within tiny chambers as small in volume as 0.4 to 1.2 $cm^3$ as in the human eye. We have discovered that two needles of one mm diameter would produce less trauma in the human body than a single 3 mm double needle. As a matter of fact, it is always desirable to simultaneously use a number of tiny needles in preference to a single large needle since, if far enough apart, the trauma caused by the tinier needles would be separately experienced and not cumulative. In any case, a dozen tiny punctures would heal much faster than a single large equivalent penetration.

The handpiece 73 may be provided with an irrigating close-off valve and an injection spincture port for applying medication directly into the chamber being invaded. It is obvious that the forceful injection of dissolvents by means of an inserted pipette will put the medicament directly into the area desired and nowhere else.

FIG. 11 illustrates a lever-type action for handpiece closure while FIG. 12 shows a roller-type closure. The handpiece 244 has a main body portion 247 which is made of plastic and has a central opening 248 formed through it, through which 1/16th inch I.D. silicon tubing 249 is inserted. On the end of opening 248, a tapered recess 252 is provided in which a collar-button type fitting 251 is placed. When a standard threaded adapter 253 is screwed into place, the entire assembly locks-up as shown and is then air and liquid tight. Lever 254 is pivotally attached to the housing 247 and is an offset type lever which when pulled backwards acts to pinch off the fluid flow by compressing the rubber tubing 249 in opening 248 at point 256.

In FIG. 12, which discloses another close-off embodiment 246 with a central opening 248 and through which tubing 249 extends, a roller 257 is slidably supported by a shaft 258 and can be moved rearward and downward to pinch off the tubing 249 at point 256 to prevent fluid flow through the tubing. Additionally a sphincture port structure 259 is provided to receive a pipette needle 264 therethrough. The injection pipette needle is sealed with a compression nut 262 and an O-ring seal 263. This needle supplies the medicament or dissolving fluid from the pipette when the pipette plunger (not shown) is depressed. This will apply the medicament under pressure to the desired location at the end of the operating needle of the handpiece 246 through tubing 249 if roller 257 is closed down.

When the handpiece 73 is used for suturing with microsurgery needles, sizes 10-0 to 5-0, use is made of a split needle holder. The needle can be picked up with the left hand, positioned correctly with the point of the right handpiece needle and placed adjacent the tissue to be sutured. A single slight burst of ultrasound, achieved by touching the foot switch briefly to on, will cause the suturing needle to vibrate at 40,000 times per second and enable it to immediately penetrate the tissue with great ease.

FIGS. 13 and 14 illustrate the control system used. In FIG. 3 it is to be noted that the switch 94 has three direct control elements 271, 272 and 273. Each separate actuating switch lever clicks on and then clicks off and no element of fatigue is present since it is not necessary to hold the foot fast against any of the switches. In the embodiment illustrated in FIG. 3, the switch 94 is hardwired by the cable 96 to the medical device 91 and the remote control ultrasonic transmission feature is not used but the same controllable items are actuated and, thus, the description of switching for both the model illustrated in FIG. 2 and FIG. 3 can be simultaneously described.

When switch 271 is pushed to the left in FIG. 2, an internal valve will activate and connect it between the pressure gauge 27 and the handpiece output fitting 81 which will now be opened and irrigation fluid will flow from the hanging bottle 18 since the hanging bottle 18 is at a higher point than gauge/adjustor 27. This static head pressure will be read on the pressure gauge part of 27 and may be set, if so desired, when running with an opened irrigating bottle. Pushing the switch 271 again will turn the treatment fluid off and so forth. The "off" condition will be noted by the pressure indicating ball in gauge 27 dropping to the bottom of its tube.

When switch 272 in FIG. 2 is lightly touched by the foot, the aspiration, which includes the vacuum pump 46, will be energized and turned on at a preset speed determined by the position of control lever 65. Thus, irrigation or aspiration or both can be selected by use of the foot by simply activating the switches 271 and 272.

The central switch 273 of the foot switches 86 and 94 in FIGS. 2 and 3 will turn the ultrasonic power to the on condition but will continue only as long as the switch 273 is depressed. Thus, power will appear at socket 71 and/or 72 depending on the position of the switch 73. When the pressure is removed from switch 273, the ultrasonic power will be disconnected from output sockets 71 and 72.

In our work in operating rooms, it has been observed that the elimination of entangling cords, tubing, wires, et al is very desirable and therefore a foot control switch which rests on the floor immediately available to the doctor's foot and which has no attachment wires is very desirable. This unique switch shown in FIG. 2 includes the switches 271, 272 and 273 but the wireless switch 86 includes an ultrasonic transmitter for radiating control signals to the medical unit 60 rather than via the hard wiring as shown in FIG. 3.

FIGS. 13 and 14 disclose the transmitter and receiver respectively, for the system.

As shown in FIG. 13, the transmitter for the remote control comprises an oscillator 282 which receives an input from a battery E and includes a monitoring meter 281 to show the condition of the battery while a movable contact 283 of a multiple switch is engageable with fixed contacts 284, 285, 286 and 287. 284 is a contact which when engaged by switch contact 283 turns oscillator 282 off. Contacts 285 through 287 energize the oscillator at different output frequencies which correspond to different control functions of the equipment. The output of the oscillator is supplied to an ultrasonic transducer 288 which radiates the energy provided by the transmitter.

FIG. 14 comprises a receiver and includes an ultrasonic transducer 291 which detects the ultrasonic energy radiated from the transducer 288 and supplies it to an amplifier 292. The output of the amplifier is supplied to a frequency detector 293 which detects a first frequency and supplies an output to control the aspirator control 297. A second frequency detector 294 detects a second control frequency and supplies an output for the irrigation control 298. A third frequency detector 295 detects a third received control frequency and supplies an output for the ultrasonic control 299. The receiver 290 may be mounted inside the medical unit and no cables need extend between the transmitter and the receiver.

FIG. 15 illustrates an electrical schematic for a transmitter using a crystal ultrasonic transducer for short range radiation. The transistor oscillator 302 receives an input from battery E while the meter 304 indicates the condition of the battery. The output of the oscillator 302 is sent through a transformer 306 having a high Q to a plurality of capacitors C30 through C33 via relays. Switches 307 and 308 are ganged together and switch 307 turns the oscillator 302 on in three positions as illustrated in FIG. 15. Switch 308 connects different valued capacitors C31 through C33 in parallel with the transformer 306 to control its frequency and the output frequencies correspond to different control functions. The transducer 303 is driven through a small capacitor C34. Typical frequencies used could be 19.25 kHz, 21.75 kHz and 23.25 kHz at approximately a 0.1 watt level or less. The meter 304 indicates when the battery E needs charging and when power is on.

The receiver is illustrated in FIG. 16 and includes a receiving transducer 307' which has one terminal grounded and the other terminal connected through a capacitor C36 and an inductance L10 which is coupled from a tapping point through another condensor to an operational amplifier 308'. Second operational amplifier 309 is in cascade with the operational amplifier 308'. Tuned indicators 311, 340 and 345 are coupled to the output of operational amplifier 309 and resonate at different frequencies and supply outputs to drive relays 320, 325 and 330 which control switches Sa, Sb and Sc respectively, which correspond to the controls associated with the respective frequencies and functions. The resonant circuit 311 comprising the capacitor C20 and inductor L10 might be tuned to frequency 19.25 kHz, which is applied to the base of the transistor 310 to drive the relay 320. The tuned circuit 340 comprising the capacitor C11 and inductor L11 may be tuned to 21.75 kHz which is applied to transistor 313 which energizes the relay 325 to actuate the switch Sb. The tuned circuit 345 comprising the capacitor C12 and the inductance L12 may be resonant at the third frequency of, for example, 23.25 kHz and this circuit supplies an output to transistor 312 which drives the relay 330 to actuate switch Sc.

It is seen that the invention provides a novel medical machine and although it has been described with respect to preferred embodiments it is not to be so limited as changes and modifications may be made which are within the full intended scope as defined by the appended claims.

We claim as our invention:

1. An ultrasonic instrument comprising an ultrasonic generator, an operating handpiece with a hollow operating tool and an ultrasonic motor in said handpiece and connected to said ultrasonic generator for operating in bio-cavities, a subsidiary pressure balancing cavity, an irrigation fluid supply separate from and connected to said balancing cavity, a first tube and a second tube connected to said balancing cavity, said balancing cavity being substantially larger than a bio-cavity to be operated within, said first tube being connected at one end to said balancing cavity and at the other end to said hollow operating tool of said handpiece, said second tube being connected at one end to said balancing cavity and the other end being adapted to be placed in fluid communication with the interior of a bio-cavity to be operated within, automatic means for accurately controlling the input fluid pressure in said balancing cavity, means for removing fluid connected to said balancing cavity at a point spaced from said fluid supply connection, said first and second tubes being connected to said balancing cavity at points located between the connection points of said fluid supply and said means for removing fluid, and one of said tubes being connected at a point closer to the fluid supply connection point than the other of said tubes.

2. An ultrasonic instrument according to claim 1 further including a control/indicating meter connected between said irrigation fluid supply and said bandpiece.

3. An ultrasonic instrument according to claim 1 including a second operating handpiece with a hollow operating tool and an ultrasonic motor in said second handpiece for operating in bio-cavities, said ultrasonic motor being connected to said ultrasonic generator, said second tube being connected to said hollow operating tool of the second handpiece and said means for removing fluid includes a suction pump connected to said balancing cavity.

4. An ultrasonic instrument according to claim 3 including negative pressure control means between said suction pump and said second handpiece.

5. An ultrasonic instrument according to claim 4 including a fluid collecting bottle connected between said suction pump and said second handpiece.

6. An ultrasonic instrument according to claim 5 including a feedback conduit connected between the irrigation fluid supply and the exhaust outlet of said suction pump.

7. An ultrasonic instrument according to claim 3 including a pressure sensing transducer connected to said subsidiary pressure balancing chamber, a drive motor connected to said suction pump, and motor speed control means receiving the output of said pressure sensing transducer and supplying an output to control the speed of said drive motor as a function of said sensed pressure.

8. An ultrasonic instrument according to claim 7 wherein said motor speed control is a voltage controlled variable frequency oscillator and said drive motor is an AC controllable motor which operates at a speed proportional to its input voltage and/or current.

9. An ultrasonic instrument according to claim 3 wherein said suction pump is a peristaltic type pump.

10. An ultrasonic instrument according to claim 3 including means for establishing a maximum preset pressure in a bio-cavity.

11. An ultrasonic instrument according to claim 3 including means for establishing a minimum preset pressure in a bio-cavity.

12. An ultrasonic device according to claim 1 including a foot actuated control means including switches for controlling irrigation, aspiration and the application of ultrasound to a handpiece.

13. An ultrasonic instrument according to claim 12 wherein said foot actuated control is hardwired to said ultrasonic generator and provides controls for said irrigating, aspirating means and making the ultrasonic energy available on demand.

14. An ultrasonic device according to claim 1 which provides ultrasonic energy to two tools.

15. An ultrasonic instrument according to claim 1 wherein a flexible tube extends through said operating handpiece and including a sphincture valve extending at an angle through said body portion to said flexible tube and sealing means for receiving a hollow needle through said sphincture valve for inserting medicant into said flexible tubing in said handpiece.

* * * * *